(12) United States Patent
Pasricha

(10) Patent No.: US 8,800,906 B2
(45) Date of Patent: Aug. 12, 2014

(54) USE OF TRANSFORMING GROWTH FACTOR-BETA NEUTRALIZING ANTIBODIES AND FUSION PROTEINS THEREOF IN TREATING PAIN

(75) Inventor: Pankaj J. Pasricha, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/337,249

(22) Filed: Dec. 26, 2011

(65) Prior Publication Data

US 2013/0011397 A1 Jan. 10, 2013
US 2014/0134167 A2 May 15, 2014

Related U.S. Application Data

(60) Provisional application No. 61/460,248, filed on Dec. 27, 2010.

(51) Int. Cl.
*C07K 16/00* (2006.01)
*C12P 21/08* (2006.01)
*A61K 39/395* (2006.01)

(52) U.S. Cl.
USPC .............. 242/158.1; 424/130.1; 424/133.1; 424/141.1; 530/387.1; 530/387.3; 530/388.1; 530/388.23

(58) Field of Classification Search
None
See application file for complete search history.

*Primary Examiner* — Christine J Saoud
*Assistant Examiner* — Jon M Lockard
(74) *Attorney, Agent, or Firm* — Stanford University; Andrea Blecken

(57) ABSTRACT

Provided herein are methods for treating pain and for reducing the excitability of nociceptors, comprising administering a TGF-β antagonist. In some embodiments, a TGF-β antagonist is a monoclonal TGF-β neutralizing antibody or a fusion product comprising a monoclonal TGF-β neutralizing antibody, a soluble receptor, an antisense oligodeoxynucleotides (ODNs), a ribozymes, a small inhibitory RNA (siRNA), Smad 6, Smad7, or a small molecule that blocks TGF-β signaling.

18 Claims, 9 Drawing Sheets

USE OF TRANSFORMING GROWTH FACTOR-BETA NEUTRALIZING ANTIBODIES AND FUSION PROTEINS THEREOF IN TREATING PAIN

RELATED APPLICATION

This application claims priority and other benefits from U.S. Provisional Patent Application Ser. No. 61/460,248, filed Dec. 27, 2010, entitled "Transforming growth factor (TGF) as a target". Its entire content is specifically incorporated herein by reference.

STATEMENT OF GOVERNMENT SUPPORT

This invention was made with government support under contract NIH R01 DK073558 awarded by the National Institutes of Health. The government has certain rights in the invention.

TECHNICAL FIELD OF THE INVENTION

The present invention relates to methods for treating pain by administration of a transforming growth factor-β (TGF-β) antagonist.

BACKGROUND

The sensation of pain functions as a natural warning sign that an injury has occurred or is about to occur and is meant to trigger a protective response. In many cases, however, the sensation of pain remains as persistent chronic inflammatory or cancer pain and becomes debilitating both physically and psychologically. Pain is the primary symptom that motivates people to seek medical treatment, accounting for over 35 million new office visits to physicians and over 70 million (80%) of all office visits to physicians each year in the United States. Pain medications are the second most frequently prescribed medications (after cardiac-renal therapeutics) during visits to physicians' offices and emergency rooms. Almost one in five adult Americans (a total of about 50 million) experiences chronic pain; 17% of patients in the United States seen by primary care physicians suffer from persistent pain; and 4.9 million people seek treatment for chronic pain each year.

As Julius and Basbaum note, pain is a complex experience that, besides the transduction of noxious environmental stimuli, also involves cognitive and emotional processing by the central nervous system (Julius D & Basbaum A I, 2001 Nature 413, 203-210).

TGF-β and other members of its superfamily including activin and bone morphogenetic proteins (BMP) are recognized as playing critical roles in the development, survival and repair of neurons in the peripheral and central nervous systems (CNS). Böttner M. et al., 2000 J. Neurochem., 75, 2227-40. However, little is known about the peripheral effects of TGF-β on nociception although its expression is increased in chronic inflammation, where it plays a key role in wound healing and promoting fibrosis. Pohlers D. et al., 2009 Biochim Biophys Acta., 1792, 746-56. Ongoing tissue injury and inflammation initiate a cascade of events resulting in peripheral sensitization, i.e., enhancement of the responsiveness of primary afferent neurons (nociceptors), whose bodies are housed in dorsal root ganglia (DRG) and whose central ends synapse with second order neurons in the spinal cord. Sensitized nociceptors display increased spontaneous activity as well as increased responsiveness to both noxious and non-noxious stimulation.

Many of the current therapies for pain unspecifically fight inflammatory agents and often have limitations in their efficacy either due to development of tolerance following a certain time period of treatment or due to undesired or even unacceptable side effects such as nausea, sedation and so forth. Consequently, there is an unmet medical need for compositions and methods for treating pain more selectively. The present invention addresses this need.

SUMMARY

Provided herein are methods for treating pain and for reducing excitability of nociceptors in order to reduce sensation of pain. In one aspect, a transforming growth factor-β (TGF-β) antagonist is administered to a subject in a therapeutically effective amount to treat pain. In some embodiments, the TGF-β agonist is a monoclonal TGF-β-neutralizing antibody. In other embodiments, the TGF-β agonist is a fusion protein (fusion product) comprising a monoclonal TGF-β neutralizing antibody and a molecule that specifically targets sensory neurons such as a monoclonal antibody against TRPV1 (anti-TRPV1), against TrkA (anti-TrkA), or against NGF (anti-NGF).

In other embodiments, the TGF-β agonist is an engineered antibody selected from the group consisting of chimeric antibodies, de-immunized antibodies, humanized antibodies, Fab or scFv antibody fragments, multimeric scFvs, and fully human antibodies. In further embodiments, the TGF-β agonist is a soluble receptor, including fusions and peptides thereof, such as the extracellular domain of the TGF-βRII or the extracellular domain of the TGF-βRIII, or fusion or peptide thereof. In yet other embodiments, the TGF-β agonist is an anti-TGF-β antisense oligodeoxynucleotide (ODN). In other embodiments, the TGF-β agonist is a ribozyme or a small inhibitory RNA (siRNA). In other embodiments, the TGF-β agonist is Smad 6 or Smad7. In other embodiments, the TGF-β agonist is a small molecule that reduces TGF-β signaling, e.g., through inhibition of the TGF-βRI kinase. In other embodiments, the TGF-β antagonist is a TGF-β1 antagonist.

In another aspect, a transforming growth factor-β (TGF-β) antagonist is administered to a subject in a therapeutically effective amount to treat pain, while at predetermined time points before and following treatment, the extent of pain relief is determined by assessing pain in the subject. In some embodiments, the TGF-β agonist is a monoclonal TGF-β-neutralizing antibody. In other embodiments, the TGF-β agonist is a fusion protein (fusion product) comprising a monoclonal TGF-β neutralizing antibody and a molecule that specifically targets sensory neurons such as a monoclonal antibody against TRPV1 (anti-TRPV1), against TrkA (anti-TrkA), or against NGF (anti-NGF).

In other embodiments, the TGF-β agonist is an engineered antibody selected from the group consisting of chimeric antibodies, de-immunized antibodies, humanized antibodies, Fab or scFv antibody fragments, multimeric scFvs, and fully human antibodies. In further embodiments, the TGF-β agonist is a soluble receptor, including fusions and peptides thereof, such as the extracellular domain of the TGF-βRII or the extracellular domain of the TGF-βRIII. In yet other embodiments, the TGF-β agonist is an anti-TGF-β antisense oligodeoxynucleotide (ODN). In other embodiments, the TGF-β agonist is a ribozyme or a small inhibitory RNA (siRNA). In other embodiments, the TGF-β agonist is Smad6 or Smad7. In other embodiments, the TGF-β antagonist is a small molecule that reduced TGF-β signaling, e.g., by inhibiting the TGF-βRI kinase. In other embodiments, the TGF-β agonist is a TGF-β1 antagonist.

In another aspect, a transforming growth factor-β (TGF-β) antagonist is administered to a subject in a therapeutically effective amount to reduce excitability of a nociceptive neuron sensing pain. In some embodiments, the TGF-β agonist is a monoclonal TGF-β-neutralizing antibody. In other embodiments, the TGF-β agonist is a fusion protein (fusion product) comprising a monoclonal TGF-β neutralizing antibody and a molecule that specifically targets sensory neurons such as a monoclonal antibody against TRPV1 (anti-TRPV1), against TrkA (anti-TrkA), or against NGF (anti-NGF).

In other embodiments, the TGF-β agonist is an engineered antibody selected from the group consisting of chimeric antibodies, de-immunized antibodies, humanized antibodies, Fab or scFv antibody fragments, multimeric scFvs, and fully human antibodies. In further embodiments, the TGF-β agonist is a soluble receptor, including fusions and peptides thereof, such as the extracellular domain of the TGF-βRII or the extracellular domain of the TGF-βRIII. In yet other embodiments, the TGF-β agonist is an anti-TGF-β antisense oligodeoxynucleotide (ODN). In other embodiments, the TGF-β agonist is a ribozyme or a small inhibitory RNA (siRNA). In other embodiments, the TGF-β agonist is Smad6 or Smad7. In other embodiments, the TGF-β antagonist is a small molecule that reduces TGF-β signaling, e.g., by inhibiting the TGF-βRI kinase. In other embodiments, the TGF-β agonist is a TGF-β1 antagonist.

In some embodiments, the pain is pain as experienced in inflammatory disease. Such inflammatory disease can be chronic or fibrotic inflammatory disease and includes, but is not limited to, rheumatoid arthritis, diabetic neuropathy, intestinal inflammation of ulcerative colitis or Crohn's disease, radiation-induced fibrosis, pancreatitis, and myocarditis.

In some embodiments, the pain is pain as experienced in cancer.

In some embodiments, the assessment of pain is carried out by subject self-report.

In certain embodiments the administering is local administration.

The above summary is not intended to include all features and aspects of the present invention nor does it imply that the invention must include all features and aspects discussed in this summary.

INCORPORATION BY REFERENCE

All publications, patent applications and patents mentioned in this specification are herein incorporated by reference to the same extent as if each individual publication or patent application was specifically and individually indicated to be incorporated by reference.

BRIEF DESCRIPTION OF THE FIGURES

The accompanying figures illustrate embodiments of the invention and, together with the description, serve to explain the invention. These figures are offered by way of illustration and not by way of limitation; it is emphasized that the various features of the drawings may not be to-scale.

Figure 1:
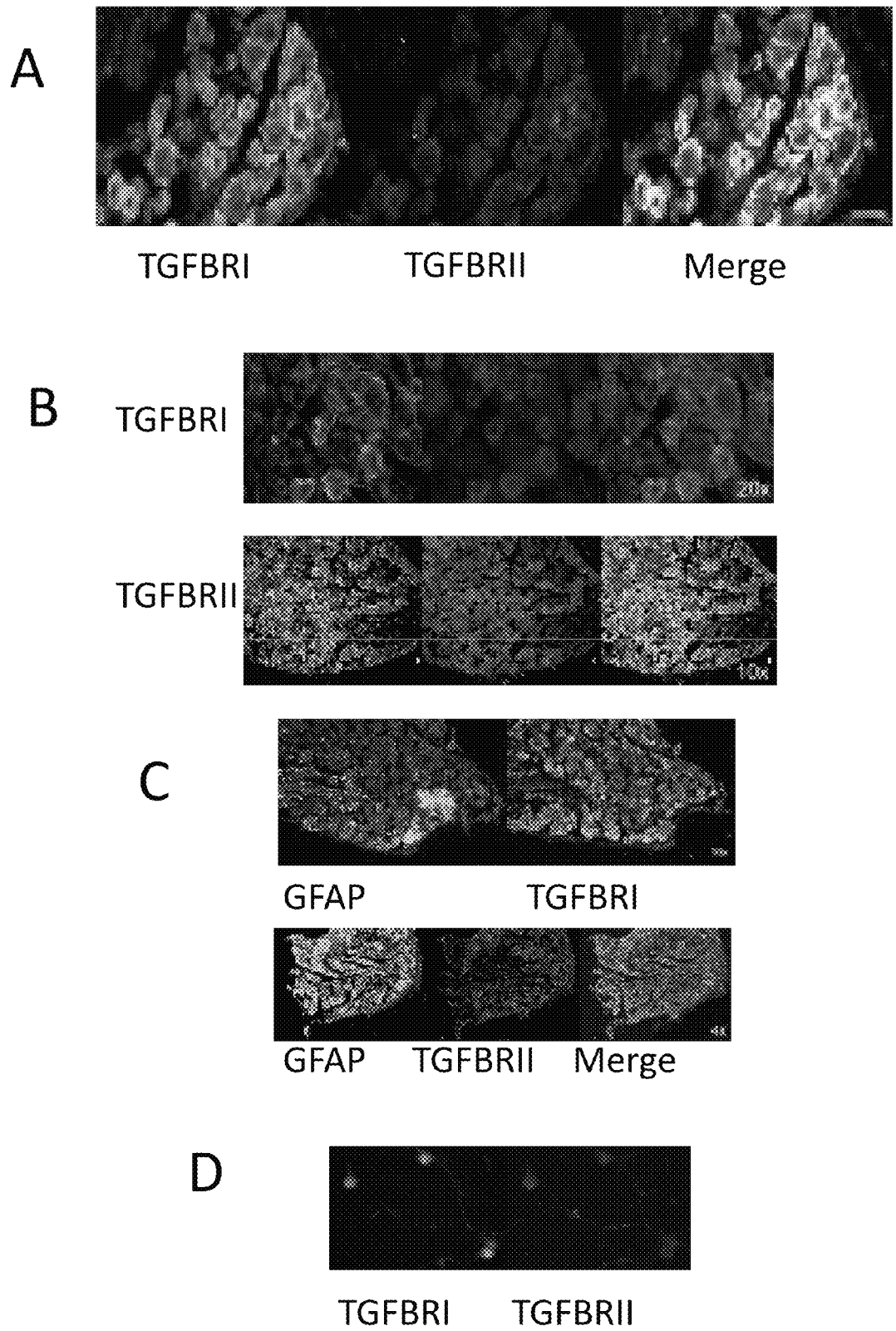
FIG. 1 illustrates that TGF-β receptors are expressed by nociceptors.

| Gene | mRNA | Protein |
|---|---|---|
| TGF-β1 | NG_013364.1 | NM_000660.4 | NP_000651.3 |
| TGF-β2 | NG_027721.1 | Variant 1 | Isoform 1 |
| | | NM_001135599.2 | NP_001129071.1 |
| | | Variant 2 | Isoform 2 |
| | | NM_003238.3 | NP_003229.1 |
| TGF-β3 | NG_011715.1 | NM_003239.2 | NP_003230.1 |
| TGF-β type I receptor | NG_007461.1 | Variant 2 | Isoform 2 |
| | | NM_001130916.1 | NP_001124388.1 |
| | | Variant 1 | Isoform 1 |
| | | NM_004612.2 | NP_004603.1 |
| TGF-β type II receptor | NG_007490.1 | Variant 1 | Isoform a |
| | | NM_001024847.2 | NP_001020018.1 |
| | | Variant 2 | Isoform b |
| | | NM_003242.5 | NP_003233.4 |
| TGF-β type III receptor | NG_027757.1 | Variant 2 | Isoform b |
| | | NM_001195683.1 | NP_001182612.1 |
| | | Variant 3 | Isoform b' |
| | | NM_001195684.1 | NP_001182613.1 |
| | | Variant 1 | Isoform a |
| | | NM_003243.4 | NP_003234.2 |

DETAILED DESCRIPTION

Before describing detailed embodiments of the invention, it will be useful to set forth definitions that are utilized in describing the present invention.

Definitions

The practice of the present invention may employ conventional techniques of chemistry, molecular biology, recombinant DNA, genetics, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. 1', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "TGF-β agonist", as used herein, relates to a molecule that inhibits the activity of TGF-β and inhibits TGF-β signaling. TGF-β agonists include, but are not limited to, ligand traps, including monoclonal TGF-β-neutralizing antibodies and soluble receptors (including fusions and peptides thereof); nucleic acid-based therapies, including antisense oligodeoxynucleotides (ODNs), ribozymes, small inhibitory RNA (siRNA), Smad 6 or Smad7; and small molecules that inhibit TGF-β signaling by, for example, blocking TGF-βRI. A TGF-β antagonist can also be a fusion protein (fusion product) comprising a monoclonal TGF-β neutralizing antibody and a molecule that specifically targets sensory neurons such as a monoclonal antibody against TRPV1 (anti-TRPV1), against TrkA (anti-TrkA), or against NGF (anti-NGF).

The term "subject", as used herein, relates to an animal, preferably a mammal, including mouse, rat, rabbit, dog, cat, guinea pig, goat, cow, horse, pig, sheep, monkey, primate, ape, and human ("human subject").

The term "therapeutically effective amount", as used herein, relates to an amount or concentration of a molecule or agent, e.g., a TGF-β agonist, that achieves a therapeutic effect in a subject, wherein the therapeutic effect can be a) an amelioration or alleviation, if not complete cessation, of pain, pain experience or sensation of pain; and b) prevention of pain, pain experience or sensation of pain.

Transforming Growth Factor-β (TGF-β)

The TGF-β family is part of a superfamily of dimeric protein growth factors that include inhibins, activins and bone morphogenic proteins. All family members carry a cluster of conserved cysteine residues that are held in a particular structure through intramolecular disulfide bonds (Blobe G C et al., 2000 N Engl J Med 342:1350-1358).

Virtually every cell in the body, including epithelial, endothelial, hematopoietic, neuronal, and connective-tissue cells, produces TGF-β and some cells have receptors for it.

TGF-β Isoforms, Receptors and Signaling Pathways

Transforming growth factor-β (TGF-β) is a ubiquitously expressed, secreted pleiotropic cytokine that exists in mammals in three isoforms TGF-β1, TGF-β2, and TGF-β3. All three TGF-β isoforms interact with the same high-affinity receptors which type I (TGF-βRI, or ALK-5), type II (TGF-βRII), and type III (TGF-βRIII, or betaglycan). The TGF-βRI and TGF-βRII receptors are signaling receptors and contain serine-threonine protein kinases in their intracellular domains that initiate intracellular signaling by phosphorylating transcription factors from the SMAD pathway; in contrast, the TGF-βRIII receptor is the only nonsignaling, but most abundant receptor (Blobe G C et al., 2000 N Engl J Med 342:1350-1358).

TGF-β is produced in a latent form consisting of TGF-β and the non-covalently bound latency-associated peptide, LAP, derived from the N-terminal of the TGF-β precursor, and must be released for activation.

TGF-β1 and TGF-β2 are produced in precursor forms of 390 and 414 amino acid residues, respectively (Derynck, R. et al., 1985 Nature 316, 701-705; de Martin, R. et al., 1987 EMBO J. 6, 3673-3677). The cDNA sequence for TGF-β3 (ten Dijke, P. et al., 1988 Proc Natl Acad Sci USA 85, 4715-4719) contains an open reading frame coding for 412 amino acids. Homodimers of the C-terminal 112 residues of TGF-β1, TGF-β2, and TGF-β3 represent the biologically active forms of these proteins. Preceding the site of cleavage to their mature forms, TGF-β1 and TGF-β2 have stretches of four and five basic residues, respectively. In TGF-β3 there are five basic residues preceding the cleavage site. The mature forms of TGF-β1 and TGF-β2 share 80/112 identical residues. The corresponding 112 C-terminal amino acids of TGF-β3 exhibit 86/112 and 89/112 identical residues compared with TGF-β1 and TGF-β2, respectively. Many remaining differences represent conservative substitutions. All three proteins show a strict conservation of the nine cysteine residues in this region.

TGF-βRIII is a protein of 853 amino acids that contains a signal sequence and large N-terminal extracellular domain followed by a transmembrane domain and a short cytoplasmic tail of 41 amino acids (Wang, X.-F. et al., 1991 Cell 67, 797-805).

TGF-βRII is a 565 amino acid protein with a signal sequence and cysteine-rich N-terminal extracellular domain followed by a transmembrane domain and a cytoplasmic serine, threonine kinase domain (Lin, H. Y. et al., 1992 Cell 68, 775-785).

TGF-βRI is a protein of 503 amino acids that contains a signal sequence and cysteine-rich N-terminal extracellular domain followed by a transmembrane domain and a cytoplasmic serine, threonine kinase domain (Franzen, P. et al., 1993 Cell 75, 681-692). The extracellular domain has little sequence similarity with the TGF-βRII receptor, but the cytoplasmic domain has more with respect to that of the TGF-βII. In the cytoplasmic domain, eleven major conserved subdomains are evident, including the ATP-binding site and the catalytic domain (Hanks, S. K., Quinn, A. M. and Hunter, T. 1988 Science 241, 42-52).

The SMAD pathway. The SMAD pathway is the canonical signaling pathway of TGF-β family members. TGF-β binds either to a type III receptor, which then presents TGF-β to a type II receptor, or TGF-β binds directly to type II receptors. Once activated by TGF-β, type II receptors recruit, bind, and transphosphorylate type I receptors which leads to the recruitment and phosphorylation of the intracellular effector proteins Smad2 and Smad3. Phosphorylated Smad2 and Smad3 subsequently bind to Smad4 and translocate to the nucleus to initiate gene expression. TGF-β signalling is negatively regulated by inhibitory Smads, including Smad6 and Smad7 (Massagué & Chen, 2000).

Apart from the SMAD pathway which encompasses Smad proteins 1-10, TGF-β affects numerous signal transduction pathways in a Smad-independent manner, such as the mitogen-activated and stress-activated protein kinase pathways (Piek E et al., 1999 FASEB J 13:2105-2124).

TGF-β Functions

TGF-β regulates the proliferation and differentiation of cells and plays an essential role in cellular functions such as apoptosis, cell cycle arrest, immune regulation, wound healing, tissue homeostasis, angiogenesis, and even cancer suppression as well as cancer growth. TGF-β is a critical molecule for many biological functions including cell growth, and can have proinflammatory as well as anti-inflammatory effects. It is produced in most if not all chronic inflammatory processes where amongst other functions, it participates in fibrosis. However, despite intense study in all other aspects of its biology, any role for TGF-β in pain that has been implicated has been inconsistent.

Apoptosis. TGF-β can induce apoptosis through the SMAD pathway or via the death associated protein 6 (DAXX adapter protein, DAXX pathway). DAXX has been shown to associate with and bind to the type II TGF-β receptor kinase.

Cell Cycle Arrest. TGF-β regulates cellular proliferation in a cell-specific manner. Proliferating cells pass through a cycle divided into four phases, G1, S, G2 and M. During the G1 phase, protein and RNA are synthesized; during the S phase, new DNA is synthesized; during the G2 phase, the newly duplicated chromosomes condense; and during the M phase, the cell undergoes mitosis to form two daughter cells. In most epithelial, endothelial, and hematopoietic cells, TGF-β is a potent inhibitor of cell proliferation. It arrests the cell cycle in the G1 phase by stimulating synthesis of the cyclin-dependent protein kinase inhibitor p15 and p21 proteins, and by inhibiting the function or production of essential cell-cycle regulators.

Immune Regulation. TGF-β is also produced by leukocytes and promotes their differentiation; it can also inhibit their proliferation and activation. In addition, TGF-β provides chemotactic stimuli for leukocyte migration and regulates adhesion molecule-mediated localization of these cells.

TGF-β as profibrotic factor involved in wound healing and synthesis of the extracellular matrix (ECM). The ECM is assembled from structural proteins and glycoproteins including collagens, laminins, glycosaminoglycans and proteoglyans, and provides structural and functional integrity to connective tissues and organs. TGF-β is a potent regulator of the production and deposition of extracellular matrix and stimulates fibroblasts and other cells to produce extracellular-matrix proteins and cell-adhesion proteins including fibronectin and integrins. TGF-β is abundantly expressed in platelets from which it is secreted in case of a tissue injury to regulate the healing process.

Tissue homeostasis, angiogenesis during embryogenesis, and role in both cancer suppression and growth. TGF-β signaling is an important regulator of tissue homeostasis and a potent growth inhibitor that also exerts cancer-suppressing activity. In normal cells, TGF-β regulates the cell cycle to stop proliferation, to induce differentiation, or to promote apoptosis. Uncontrolled growth is a necessary step for the development of all cancers. When a cell is transformed into a cancer cell, perturbations and defects in the TGF-β signaling pathway, that result from mutation in Ras genes and activation of the MAP/ERK pathway, lead to uncontrolled growth, and TGF-β loses its growth-inhibitory and apoptosis-inducing effects on cancer cells and instead supports their proliferation, among others, through its angiogenetic effects. Cancer cells often secrete excess TGF-β and respond to it by enhanced tissue invasion and metastasis.

TGF-β Antagonists

Several inhibitors of various components of the TGF-β pathway have been contemplated and developed. Korpal, M. and Kang Y., 2010 Eur J Cancer 46, 1232-1240; Bonafoux, D. and Wen-Cherng, L. 2009 Expert Opin Ther Patents 19, 1759-1769; Prudhomme, G. J., 2007 Laboratory Investigation 87, 1077-1091. These antagonists fall into three major classes: (a) ligand traps, including monoclonal TGF-β-neutralizing antibodies and soluble receptors (including fusions and peptides thereof); (b) nucleic acid-based therapies, including antisense oligodeoxynucleotides (ODNs), ribozymes, small inhibitory RNA (siRNA), Smad6 or Smad7; and (c) small molecules that inhibit TGF-β signaling by, for example, blocking TGF-βRI. In certain embodiments, such molecules can be orally active and cross the blood-brain barrier; in other embodiments, such molecules must be administered systemically.

Neutralizing antibodies minimize interactions between ligands and receptors. One neutralizing assay is the neutralization of the growth inhibitory activity of TGF-β1, TGF-β2, and TGF-β3 in vitro on mink lung MvlLu epithelial cells. Lucas, C. et al., 1990 J. Immunol. 145, 1415-1422. Neutralizing antibodies, such as 2G7 and 1D11, can bind and reduce the biological activity of all three TGF-β ligands; 2G7 and 1D11 both have a preclinical effect, whereas the non-neutralizing 12H5 has no such pre-clinical effect. Arteaga, C. L. et al., 1993 J Clin Invest 92, 2569-76; Pinkas, J. and Teicher, B. A. 2006 Biochem Pharmacol 72, 523-9; Nam, J. S. et al., 2006 Cancer Res 66, 6327-35; Ananth, S. et al., 1999 Cancer Res 59, 2210-6. GC1008, a humanized TGF-β-neutralizing monoclonal antibody is capable of neutralizing all three TGF-β isoforms, and has a Phase 1/II clinical effect. Morris, J. et al., 2008 J Clin Oncol 26 (Abstract #9028); Tan, A. R., Alexe, G., and Reiss, M. 2009 Breast Cancer Res Treat 115, 453-95.

Similar to neutralizing antibodies, soluble receptors also function as ligand traps, minimizing functional ligand-receptor interactions. The extracellular domain of the TGF-βRII (Muraoka, R. S. et al., 2002 J Clin Invest 109, 1551-9) and the extracellular domain of the TGF-βRIII (Bandyopadhyay, A. et al., 2002 Cancer Res 62, 4690-5) have been shown to have a preclinical effect.

Antisense-mediated inhibition of TGF-β1 gene expression has been shown to be effective in preclinical trials, with AP12009 being at an advanced stage of clinical development. Schlingensiepen, K. H. et al., 2008 Recent Results Cancer Res 177, 137-50.

Another strategy aimed at minimizing ligand-receptor interactions is focused at directly blocking the catalytic activity of the TGF-β receptor kinase. SD-208 is a small molecule inhibitor of the ATP binding site of the TGF-βRI kinase shown to have a preclinical effect. Bonniaud, P. et al., 2005 Am J Respir Crit. Care Med 171, 889-98; Uhl, M. et al., 2004 Cancer Res 64, 7954-61; Ge, R. et al., 2006 Clin Cancer Res 12, 4315-30. Ki26894 is a small molecule TGF-βRI kinase inhibitor shown to have a preclinical effect. Ehata, S. et al., 2007 Cancer Sci 98, 127-33. LY2109761 is a small molecule TGF-βRI and TGF-βRII dual inhibitor shown to have a preclinical effect. Melisi, D. et al., 2008 Mol Cancer Therapy 7, 829-40; Zhang, B. et al., 2009 Cancer Lett 277, 114-20. LY2157299 is a small molecule TGF-βRI kinase inhibitor entering Phase I clinical trials. Calvo-Aller, E. B. J. et al., 2008 J Clin Oncol 26 (Abstract #14554).

The small molecule SIS3 (6,7-dimethyl-2-[(2E)-3-(1-methyl-2-phenyl-1H-pyrrolo[2,3-b]pyridin-3-yl-prop-2-enoyl)-1,2,3,4-tetrahydroisoquinoline hydrochloride) was described by Jinnin et al., (Jinnin M. et al., 2006, Mol Pharmacol 69: 597-607) as a specific inhibitor of Smad3 that suppresses Smad3 phosphorylation, DNA-Smad3 binding, and the interaction of Smad3 with Smad4. It does not affect the phosphorylation of Smad2, the expression of Smad4 or Smad7, or the phosphorylation of other signaling pathways, such as p38, p85, or ERK. In these studies, SIS3 blocked excessive production of extracellular matrix from TGF-β1-treated normal fibroblasts and scleroderma fibroblasts, an in-vitro model of autocrine TGF-β signaling.

Laping, N J et al., (Laping, N J et al., 2002, Mol Pharmacol 62:58-64) reported about the selective inhibition of Smad3 phosphorylation and, consequently, inhibition of TGF-β-induced nuclear Smad3 localization through the small molecule SB-431542.

Another group of small molecules that has gained attention as potential TGF-beta antagonists pertains to Angiotensin-II receptor antagonists such as losartan. These were found effective in stopping progression of aortic disease in Marfan Syndrome, a connective tissue disorders (Habashi, J. P. et al., 2006, Science 312:117-121).

Pain Pathways

Cutaneous and deep somatic tissues are innervated by primary afferent neurons that synapse with second-order neurons in the dorsal horn of the spinal cord. Primary afferent neurons have three functions with respect to their role in nociception: (1) detection of noxious or damaging stimuli (transduction); (2) passage of the resulting sensory input from peripheral terminals to the spinal cord (conduction); and (3) synaptic transfer of the sensory input to neurons within specific laminae of the dorsal horn (transmission). Sensory information arising from noxious stimuli is then passed on to supraspinal structures including the thalamus and the brainstem. Kidd, B. L. and Urban L. A., 2001 J. Br. Anaesth. 87, 3-11.

A series of ion-channel-linked receptors is known which mediates various sensations ranging from sensation of pain, hotness, warms, coldness, pressure to sensory transduction of noxious stimuli; these include transient receptor potential (TRP) channels such as the vanilloid receptors and others sensitive to protons/cations, including sodium, calcium and magnesium. TRP channels are ubiquitously expressed in many cell types and tissues and are primarily located on the plasma membrane. Mammalian TRP channels are activated and regulated by a wide variety of stimuli which include molecules found in spices such as capsaicin.

The transient receptor potential Vanilloid receptor 1 (TRPV1) responds to multiple pain-producing stimuli and is primarily distributed in small diameter afferent neurons. TRPV1 is activated by protons and, therefore, its activity might be enhanced within the acidic environment of inflamed tissues.

Nerve growth factor (NGF) plays as a neurotrophic factor an essential role for the survival of sensory and sympathetic neurons during embryonic development. In the adult, NGF has been found to play an important role in nociceptor sensitization after tissue injury and to regulate a host of ion channels, receptors, and signaling molecules to enhance acute and chronic pain. Upon binding to its cognate receptor, tropomyosin-related kinase A receptor (TrkA), the NGF-TrkA complex is internalized and transported from peripheral nerve endings to sensory cell bodies in the dorsal root ganglion (DRG) leading to sensitization of primary afferent nociceptors to thermal and chemical stimuli and increased expression of receptors and channels at the membrane surface, including TRPV1, acid-sensing ion channels 2 and 3, endothelin receptors, bradykinin receptors, voltage-gated sodium, and calcium channels that contribute to immediate hypersensitivity after inflammation. In addition, NGF is known to be released by inflammatory cells including eosinophils, lymphocytes, macrophages and mastcells. Mantyh, P. W. et al. 2011, Anesthesiology 115, 189-204.

Transforming Growth Factor-β (TGF-β) Antagonists for Use in Treating Chronic Inflammatory or Cancer Pain and for Reducing Excitability of Nociceptive Neurons Sensing Pain (Nociceptors)

Transforming growth factor-β (TGF-β) is a critical molecule for many biological functions including cell growth and inflammation. It is produced in most if not all chronic inflammatory processes where amongst other functions, it participates in fibrosis. Despite intense study in all other aspects of its biology, any role for TGF-β in pain that has been implicated has been inconsistent. As conclusively demonstrated by the inventor herein, transforming growth factor-β (TGF-β) plays a significant role in pain. Targeting this molecule by molecules that block its action therefore represents an original approach to the treatment of pain and provides the basis for an entirely new class of analgesics.

While post-translational changes in key ion channels and receptors underlie the immediate/acute phase of sensitization, sustained/chronic peripheral sensitization is also accompanied by neuroplastic transcriptional events. These changes are induced by various components of the inflammatory milieu including physico-chemical factors (e.g., temperature, acid) as well as a variety of small molecules, cytokines, growth factors, other peptides and enzymes that are a hallmark of chronic inflammation. Cheng J. K. and Ji R. R., 2008 Neurochem Res., 33, 1970-8.

Although TGF-β is prominent amongst these factors, its participation in nociceptive sensitization has received little attention, with what little attention it has received creating a conflict in the literature. E.g., Echeverry, S. et al., 2009 Mol Pain 5: 16; Tramullas, M. et al., 2010 J. Neurosci. 30: 1502; and Farr M. et al., 1999 Learn Mem., 6, 331.

In one aspect, provided herein are methods for treating pain via the administration of a transforming growth factor-β (TGF-β) antagonist. It is demonstrated in the examples provided herein that the administration of a monoclonal TGF-β neutralizing antibody, as one embodiment of a TGF-β agonist, to mice alleviated pain in chronic pancreatitis, a condition that is associated with fibrosis and pain.

In another aspect, provided herein are methods for reducing excitability of a nociceptive neuron sensing pain via the administration of a transforming growth factor-β (TGF-β) antagonist. It is demonstrated in the examples provided herein that the administration of a monoclonal TGF-β neutralizing antibody, as one embodiment of a TGF-β agonist, reduced excitability of isolated sensory neurons in vitro. In further examples, it is demonstrated herein that the TGFβRI/ALK5 kinase inhibitor SB431542 and the SMAD3 inhibitor SIS3, as further embodiments of TGF-β agonists, prevented a decrease in resting membrane potential induced by TGF-β.

Fusion products with a TGF-β agonist are also contemplated and are understood to be included in the definition of a TGF-β agonist. For example, the monoclonal TGF-β neutralizing antibody can also be administered as a fusion protein together with a molecule that specifically targets sensory neurons such as a monoclonal antibody against TRPV1 (anti-TRPV1), against TrkA (anti-TrkA), or against NGF (anti-NGF).

Assessing Pain in Human Subjects

Pain can be classified along a continuum of duration, as acute (of relatively brief duration) or chronic (persists for extended periods of time). Another way to classify pain is based on diagnosis, e.g., pain in inflammatory disease. Yet another continuum used to classify pain is one based on the ages of the individual suffering from pain.

Pain and suffering are private, internal events that are inherently subjective. Assessment of pain in human subjects is therefore frequently built upon the use of self-reports. Four dimensions or categories of the pain experience can be assessed in nearly all pain patient populations: pain intensity, pain affect, pain quality, and pain location. Jensen, M. and Karoly, P. In: Turk D, and Melzack R., editors. Handbook of pain assessment. $2^{nd}$ ed. New York, N.Y.: Guilford Pres, 2001, p. 15-34. Relief from pain as a consequence of successful treatment can be determined by assessing pain in a human subject at predetermined time points prior and after treatment with a TGF-β agonist, and comparing the human subject's pain assessments prior and after treatment. For example, pain can be assessed in the human subject by self-report anytime prior to treatment with a TGF-β agonist, e.g., 15 minutes prior, 30 minutes prior, 45 minutes prior, 1 hour prior, 2 hours prior and so forth, and following treatment with a TGF-β antagonist, e.g., 1 minute following treatment, 5 minutes, 15 minutes, 30 minutes, 45 minutes, 1 hour, 2 hours, 4 hours, 8 hours following treatment and so forth. When the comparative pain assessment results in a decrease of pain, e.g., a decrease in pain intensity, pain affect, pain quality and/or pain location, then the pain treatment in the human subject can be deemed successful, and vice versa.

Pain intensity. Pain intensity is a quantitative estimate of the magnitude and severity of perceived pain. The three most commonly used methods to assess pain intensity are Verbal Rating Scales (VRSs), Visual Analogue Scales (VASs), and Numerical Rating Scales (NRSs). Less common measures include various versions of a picture (or face) scale, and the Descriptor Differential Scale of Pain Insensity (DDS-I).

A VRS is composed of a list of adjectives describing different levels of pain reflecting the extremes of this dimension (e.g., from "no pain" to "extremely intense pain"), from which patients select the adjective that best describes their level of pain. A VAS is constituted by a line whose ends are labeled as the extremes of pain (e.g., "no pain" to "pain as bad as it could be"). A NRS involves asking patients to rate their pain on a numerical scale from 0 to 10 (or 100), with the understanding that the 0 represents one end of the continuum (i.e., no pain) while the 10 (or 100) represents the other extreme of pain (i.e., pain as bad as it could be). Picture or face scales employ photographs or drawings that illustrate facial expressions of persons experiencing different levels of pain. A DDS-I instructs patients to rate their sensation in relation to a descriptor on a list describing different levels of pain.

Pain affect. Pain affect may be defined as the emotional arousal and feelings engendered by the pain experience. The most widely used measure of pain affect is the Affective subscale of the McGill Pain Questionnaire (MPQ). Four additional methods of assessing pain affect are VRSs, VASs, the Descriptor Differential Scale of Pain Affect (DDS-A), and the Affective subscale of the Pain-O-meter (POM).

The MPQ consists primarily of 3 major classes of word descriptors—sensory, affective and evaluative—that are used by patients to specify their pain experience. It also contains an intensity scale and other items to determine the properties of pain experience. Melzack, R. 1975 Pain 1, 277-99. A short form of the McGill Pain Questionnaire (SF-MPQ) has been developed. Melzack, R. 1987 Pain 30, 191-7.

Similar to VRSs for pain intensity, VRSs for pain affect are composed of a list of adjectives describing different degrees of discomfort and unpleasantness. VASs for pain affect are like VASs for pain intensity; only the endpoint labels are different. The DDS-A is similar to the DDS-I, but uses different descriptors. A POM includes a mechanical VAS and two lists of pain adjectives, which are subsets of words selected from the MPQ.

Pain quality. Pain quality refers to the sensations associated with pain. The MPQ, SF-MPQ, and Neuropathic Pain Scale (NPS) are the primary measures of this component. The NPS is like the MPQ or SF-MPQ, but the items are scored individually. The MPQ and SF-MPQ Sensory scales, instead, are scored to create global estimates of sensory pain.

Pain location. Pain location can be defined as the perceived location(s) of pain that patients experience on their bodies. The instrument most commonly used to assess pain location is the pain drawing, usually involving a drawing of the front and back of the human body. Patients are asked to locate the location of their pain on the surface of the drawings.

Animal Models of Nociception for Assessing Pain in Subjects Other than Human Subjects In non-human subjects, relief from pain as a consequence of successful treatment can be determined by assessing pain following a nociceptive mechanical stimulus in the non-human subject at predetermined time points prior and after treatment with a TGF-β agonist using an animal model of nociception, and comparing the non-human subject's pain assessments with the animal model of nociception prior and after treatment. For example, pain can be assessed following a nociceptive mechanical stimulus in the non-human subject anytime prior to treatment with a TGF-β agonist, e.g., 15 minutes prior, 30 minutes prior, 45 minutes prior, 1 hour prior, 2 hours prior and so forth, and following treatment with a TGF-β agonist, e.g., 1 minute following treatment, 5 minutes, 15 minutes, 30 minutes, 45 minutes, 1 hour, 2 hours, 4 hours, 8 hours following treatment and so forth. When the comparative pain assessment results in a decrease of pain, e.g., a decrease in pain intensity, pain affect, pain quality and/or pain location, then the pain treatment in the non-human subject can be deemed successful, and vice versa.

Nociception is the activation of sensory transduction in receptors that convey information about tissue injury. There are some models of chronic pain in animals such as the rat with induced arthritis and rats that have had various lesions to the central or peripheral nervous systems. Most models are of acute pain. Animal models (usually rodents) of acute nociception use short duration stimuli ("phasic pain") or long duration stimuli ("tonic pain"). Le Bars, D., Gozariu, M. and Cadden, S. W. 2001 Pharmacol Rev 53, 597-652.

The most commonly used are animal models of short duration stimuli. Some tests are based on the use of thermal stimuli. First is the tail-flick test. One variant of this test involves applying radiant heat to a spot on the tail. The other variant of the tail-flick test uses immersion of the tail. The application of thermal stimuli provokes withdrawal of the tail. It is the reaction time of this movement that is recorded. Second is the paw withdrawal test, which substitutes the paw for the tail. Third is the hot plate test. This test introduces a rodent onto a floor that is heated. This produces reflex withdrawal, which can be measured in terms of reaction time. Finally, tests using cold stimuli are inspired by those that use heat by contact: immersion of the tail or a limb, or placing the animal on a cold surface.

Some tests are based on the use of mechanical stimuli. The preferred sites to apply nociceptive mechanical stimuli are the hind paw and tail. In the course of such a test, a pressure of increasing intensity is applied. The measured parameter is the threshold for the appearance of the reflex withdrawal of the hind paw or tail.

Some tests are based on the use of electrical stimuli. Electrical stimulation can be delivered in the form of long-lasting trains to the tail through electrodes. Measurements are made of the threshold for the reflex movement of the tail. Electrical stimulation can instead be delivered in the form of long-lasting trains to the paw through the floor of the cage in which the animal is free to move. Measurements are made of the threshold for the animal twitching or jumping (the "flinch-jump" test).

Electrical stimulation can alternatively be delivered in the form of single shocks or very short trains to the tail through electrodes. The observed behavior is related to that observed with long-lasting trains. Electrical stimulation can rather be delivered in the form of pulp stimulation. The type of response that is monitored is the appearance of the reflex movement of the head or jaw. Electrical stimulation can otherwise be delivered by stimulation of the limbs to obtain electromyographic recordings.

Turning to animal models of long duration stimuli, these tests involve using a chemical agent as the nociceptive stimulus. The main types of behavioral test based on such stimuli use intradermal or intraperitoneal injections. The most commonly used substance for intradermal injections is formalin (the "formalin test"). Usually, the formalin is injected in the forepaw to provoke a painful behavior that can be assessed on a scale related to the behavior. Alternatively, the intraperitoneal injection of agents provokes a stereotyped behavior so that the test is sometimes called the abdominal contortion test, but more commonly it is known as the "writhing test." The measurements are generally of the occurrence per unit time of the contortions resulting from the injection of the agent. In addition to such tests, other tests are based on the stimulation of hollow organs. These animal models can be split into two categories on the basis of the stimulus type: those involving the administration of chemical agents and those involving distension of hollow organs.

Electrophysiology and Neural Cell Culture

Patch Clamping: An Introductory Guide to Patch Clamp Electrophysiology, by Areles Molleman, 2003, is a useful guide for patch clamp electrophysiology. Neural Cell Culture: A Practical Approach, by Wilkin Cohen, 1996, and Protocols for Neural Cell Culture, by Laurie C Doering, 2009, are useful references for neural cell culture.

Chronic Pain in Inflammatory Disease or Cancer

The action of TGF-β following inflammatory responses is characterized by increased production of extracellular matrix (ECM) components, as well as mesenchymal cell proliferation, migration, and accumulation. Pohlers D. et al., 2009 Biochim Biophys Acta., 1792, 746-56. TGF-β is thus important for the induction of fibrosis often associated with chronic phases of inflammatory diseases. This common feature of TGF-related pathologies is observed in many different organs and diseases, e.g., rheumatoid arthritis, diabetic neuropathy, intestinal inflammation of ulcerative colitis and Crohn's disease, radiation-induced fibrosis, pancreatitis, and myocarditis. Due to its central role in inflammatory diseases, and based on its mediation of pain, TGF-β remains an attractive therapeutic target, in some instances especially if targeted locally and during the chronic or fibrotic phase of inflammatory disease.

Increased TGF-β production in several kinds of cancer diseases may activate sensory neurons and sensitize nociceptors and, thus, is considered to contribute to the experienced pain in cancer diseases such as gastrointestinal cancers including colorectal cancer and pancreatic cancer. Kaklamani, V. G. and Pasche, B. 2004, Exp Rev Antican Ther 4, 649-661; Lu, Z. et al. 1997, Dig Dis Sci 42, 2054-63.

Administration, Dosages, Dosing Regimens and Formulations

The dosage and dosing regimen for the administration of a TGF-β agonist for treating pain and/or for reducing the excitability of nociceptors, as provided herein, is selected by one of ordinary skill in the art, in view of a variety of factors including, but not limited to, age, weight, gender, and medical condition of the subject, the severity of the pain that is experienced, the route of administration (oral, systemic, local), the dosage form employed, and may be determined empirically using testing protocols, that are known in the art, or by extrapolation from in vivo or in vitro tests or diagnostic data.

The dosage and dosing regimen for the administration a TGF-β agonist, as provided herein, is also influenced by toxicity in relation to therapeutic efficacy. Toxicity and therapeutic efficacy can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Molecules that exhibit large therapeutic indices are generally preferred.

The effective dose of a TGF-β agonist, can, for example, be less than 50 mg/kg of subject body mass, less than 40 mg/kg, less than 30 mg/kg, less than 20 mg/kg, less than 10 mg/kg, less than 5 mg/kg, less than 3 mg/kg, less than 1 mg/kg, less than 0.3 mg/kg, less than 0.1 mg/kg, less than 0.05 mg/kg, less than 0.025 mg/kg, or less than 0.01 mg/kg. Doses of a TGF-β antagonist, administered to a subject as provided in the methods herein can, for example, be between about 0.001 mg/kg to about 50 mg/kg. In certain embodiments, the effective dose is in the range of, for example, 0.005 mg/kg to 10 mg/kg, from 0.01 mg/kg to 2 mg/kg, or from 0.05 mg/kg to 0.5 mg/kg. In various embodiments, an effective dose is less than 1 g, less than 500 mg, less than 250 mg, less than 100 mg, less than 50 mg, less than 25 mg, less than 10 mg, less than 5 mg, less than 1 mg, less than 0.5 mg, or less than 0.25 mg per dose, which dose may be administered once, twice, three times, or four or more times per day. In certain embodiments, an effective dose can be in the range of, for example, from 0.1 mg to 1.25 g, from 1 mg to 250 mg, or from 2.5 mg to 1000 mg per dose. The daily dose can be in the range of, for example, from 0.5 mg to 5 g, from 1 mg to 1 g, or from 3 mg to 300 mg.

The TGF-β agonist may be administered in a single daily dose, or the total daily dose may be administered in divided doses, two, three, or more times per day. In some embodiments, the dosing regimen is maintained for at least one day, at least two days, at least about one week, at least about two weeks, at least about three weeks, at least about one month, or longer. In some embodiments, an intermittent dosing regimen is used, i.e., once a month, once every other week, once every other day, once per week, twice per week, and the like. In some embodiments, the compound is administered at least once daily for at least five consecutive days.

The TGF-β agonist can be administered to the subject as a pharmaceutical composition that includes a therapeutically effective amount of the TGF-β agonist in a pharmaceutically acceptable vehicle. It can be incorporated into a variety of formulations for therapeutic administration by combination with appropriate pharmaceutically acceptable carriers or diluents, and may be formulated into preparations in solid, semi-solid, liquid, or gaseous forms, such as tablets, capsules, powders, granules, ointments, solutions, suppositories, injections, inhalants, gels, microspheres, and aerosols.

In some embodiments, the TGF-β agonist can be formulated as a delayed release formulation. Suitable pharmaceutical excipients and unit dose architecture for delayed release formulations may include those described in U.S. Pat. Nos. 3,062,720 and 3,247,066. Delayed release formulations can be formulated in tablets that can be coated using known methods to achieve delayed disintegration in the gastrointestinal tract of a human. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Oral compositions that specifically release orally-administered agents in the small or large intestines of a human subject can be made using known technology. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon. See Hardy et al. 1987 Aliment Pharmacol. Ther. 1:273-80. Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend & Chang 1984 J. Med. Chem. 27:261-6) and a variety of naturally available and modified polysaccharides (see PCT application PCT/GB89/00581) can be used in such formulations.

In other embodiments, the TGF-β agonist can be formulated as a sustained release formulation. Suitable pharmaceutical excipients and unit dose architecture for sustained release formulations include those described in U.S. Pat. Nos. 3,062,720 and 3,247,066. The TGF-β antagonist can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly(ε-caprolactone) and poly(alkylene oxide) (U.S. 20030068384) to create a sustained release formulation. Such formulations can be used in implants that release an agent over a period of several hours, a day, a few days, a few weeks, or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and US20020019446. In such sustained release formulations microparticles of drug are combined with microparticles of polymer. One or more sustained release implants can be placed in the large intestine, the small intestine, or both. U.S. Pat. No. 6,011,011 and WO 94/06452 describe a sustained release formulation providing either polyethylene glycols (where PEG 300 and PEG 400 are most preferred) or triacetin. WO 03/053401 describes a formulation that may both enhance bioavailability and provide controlled release of the agent within the GI tract. Additional sustained release formulations are described in WO 02/38129, EP 326 151, U.S. Pat. No. 5,236,704, WO 02/30398, WO 98/13029; U.S. 20030064105, U.S. 20030138488A1, U.S. 20030216307A1,U.S. Pat. No. 6,667,060, WO 01/49249, WO 01/49311, WO 01/49249, WO 01/49311, and U.S. Pat. No. 5,877,224.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients, and the like. The compositions can also include additional substances to approximate physiological conditions, such as pH adjusting and buffering agents, toxicity adjusting agents, wetting agents, and detergents. The composition can also include any of a variety of stabilizing agents, such as an antioxidant for example. Tablet formulations can comprise a sweetening agent, a flavoring agent, a coloring agent, a preservative, or some combination of these to provide a pharmaceutically elegant and palatable preparation.

Further guidance regarding formulations that are suitable for various types of administration can be found in Remington's Pharmaceutical Sciences, Mace Publishing 20 Company, Philadelphia, Pa., 17th ed. (1985).

For oral administration, the TGF-β agonist can be administered in solid dosage forms, such as capsules, tablets, and powders, or in liquid dosage forms, such as elixirs, syrups, and suspensions. The compound can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Administration

The TGF-β agonist may be administered to a subject using any convenient means capable of resulting in the desired treatment of pain. Routes of administration include, but are not limited to, oral, rectal, parenteral, intravenous, intracranial, intraperitoneal, intradermal, transdermal, intrathecal, intranasal, intracheal, intracapillary, subcutaneous, subdermal, topical, intramuscular, injection into the cerebrospinal fluid, injection into the intracavity, or injection directly into the brain. Oral administration can include, for instance, buccal, lingual, or sublingual administration. The TGF-β agonist may be systemic after administration or may be localized by the use of local administration, intramural administration, or use of an implant that acts to retain the active dose at the site of implantation. For a brief review of methods for drug delivery see Langer, 1990 Science 249:1527-1533.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXAMPLES

The following examples are put forth so as to provide those of ordinary skill in the art with a complete disclosure and description of how to make and use the present invention; they are not intended to limit the scope of the invention as it is defined by the specification and the appended claims. All references cited in this specification are incorporated herein by reference. Unless indicated otherwise, part are parts by weight, molecular weight is average molecular weight, temperature is in degrees Centigrade, and pressure is at or near atmospheric.

Example 1

TGF-β Induces Sensory Neuronal Hyperexcitability, Pancreatic Pain and Hyperalgesia in Rats with Chronic Pancreatitis, a condition with Fibrosis and Pain; Blockade of TGF-β Reduces Pain This example shows that the administration of TGF-β causes sensory neuronal Hyperexcitability, pancreatic pain and hyperalgesia in rats with chronic pancreatitis. It further demonstrates that this pancreatic pain was reduced upon administration of a TGF-β agonist, which was in this embodiment a monoclonal TGF-β neutralizing antibody.

Materials and Methods.

Care and handling of these animals were approved by the Institutional Animal Care and Use Committee at Stanford University in accordance with the guidelines of the International Association for the Study of Pain.

Intrapancreatic infusion of TGF-β. Rats were anesthetized with sodium nembutal (Abbott Laboratories, Chicago, Ill.) (50 mg/kg body weight, i.p.). The peritoneum was incised to expose the duodenum, and the duodenal loop was pulled out. The pancreatic duct entering the duodenum was identified under dissecting microscope, and a small niche was made into the duct with a 30-gauge needle. A polyethylene 10 tubing (0.61 mm outer diameter) (Becton Dickinson and Company, Franklin Lakes, N.J.) was guided into the duct and tied to secure its position. The position of the tube in the pancreatic duct was confirmed by observing bile flowing through the tubing. The common bile duct was ligated close to the liver to prevent entry of the injected substance into the liver. Similarly the duct was ligated near its entry into the duodenum. Four hundred μl (0.4 ml) per rat of 400 ng of TGF-β1 or TGF-β2 in 10% ethanol in phosphate buffered saline (PBS) or vehicle alone was injected through a syringe connected to the tubing. The tubing was carefully removed and bile flow from the liver into the duodenum was re-established. The abdominal cavity was closed with sutures and rats allowed to recover.

FOS Immunochemistry. Eight rats were used for this experiment (TGF-β n=4; Vehicle n=4). TGF-β2 (400 ng) in 0.4 ml of 10% ETOH/PBS or vehicle alone were infused into pancreatic duct of rats. 24 hours later rats underwent noxious electrical stimulation of the pancreas (5 mA for 5 minutes). Thirty minutes later the rats were transcardially perfused with 150 ml of normal saline followed by ice cold 400 ml of 4% paraformaldehyde in 0.1M phosphate buffer (PB) pH 7.4. Spinal cord segments corresponding to DRG T8-T10 were identified, cut and post-fixed in 4% paraformaldehyde over night. The samples were then transferred to 30% sucrose in 0.1 M PB for 24 hours at 4° C. followed by freezing on dry ice with optimum cutting temperature (OCT). Frozen serial coronal sections (35 μm) were cut on a cryostat, collected in separate wells of a 24-well plate and stored floating in anti-freeze at −20° C. We processed a total of 6 sections per segment. The sections were stained with a rabbit polyclonal primary antiserum directed against FOS (ab7963, Abcam, Cambridge Mass.), diluted (1:2000) in PB saline containing 3% normal goat serum and 0.1% Triton X-100, for 24 h at 4° C. Antibody staining was visualized with biotinylated goat anti-rabbit IgG (1:1000) and avidin-biotin peroxidase complex (Vector Labs Inc., Burlingame, Calif.) with hydrogen peroxide and diaminobenzidine (DAB) as substrate. Sections were mounted on superfrost/plus slides and dehydrated. The number of FOS positive cells in spinal cord laminae I/II were counted under 40× magnification from 6 slices per individual spinal segment per animal by two blinded investigators.

Induction of Chronic Pancreatitis in Rats. The pancreatic duct was accessed as described above, and 0.5 ml of a 2% solution of trinitrobenzene sulfonic acid (TNBS), in 10% ethanol in PBS, pH 7.4, was infused over a period of 2 to 5 minutes at a pressure of 50 mmHg. After a 30 minutes exposure to TNBS, needle and tubing were removed, the hole in the duodenum was sutured and the vascular clamp was removed restoring bile flow. Rats underwent further intervention at three weeks at which time a robust chronic pancreatitis had developed, as described in Winston, J. H. et al., 2005 Pain 117, 214-22.

Behavioral Studies of Rats with Chronic Pancreatitis. At the time of surgery for intrapancreatic infusion, a pair of electrodes was attached to the pancreas and externalized behind the head, as described in Winston, J. H. et al., 2005 Pain 117, 214-22, and the rats allowed to recover. At specified times subsequently, rats were given successive applications of current at 2, 5 and 10 mA for 5 min with 10 min rest between stimulation periods. The number of nocifensive behaviors observed during 5 min of stimulation period was counted. Behaviors consisted of stretching, licking of the limbs and abdomen, contraction of abdominal wall muscles and extension of the hind limbs.

Von Frey Filament (VFF) testing was performed, as described in Winston, J. H. et al., 2005 Pain 117, 214-22. Briefly, prior to testing, the belly was shaved and areas designated for stimulation were marked in relation to fore and hind limbs. Rats were placed in a plastic cage with a mesh floor and were given 30 min to adapt before testing. VFF of various calibers (Stoelting, Wood Dale, Ill.) were applied in ascending order to the designated abdominal area 10 times each for 1-2 s with a 10 s interval between applications. A positive response was considered when the rat raises its belly (withdrawal response). The data were expressed as a percentage of the number of positive responses with each filament for each rat. All the tests were performed in a blinded manner.

Blockade of TGF-β. Three weeks after infusion of TNBS, we injected a monoclonal TGF-β-neutralizing antibody (MAB 240, R&D Systems, Minneapolis, Md.) in a single dose of 1 mg/kg intraperitoneally to a group of rats (n=4). Control rats (n=4) were injected with the same dose of another antibody to TGF-β, but one without neutralizing properties (MAB 2401, R&D Systems, Minneapolis, Md.). One week after the injection, rats underwent testing for pain behavior.

Dorsal Root Ganglia (DRG) neurons culture. Adult Sprague-Dawley rats (120-150 g) were sacrificed by decapitation. Thoracic and lumbar DRGs were then bilaterally dissected out and transferred to ice-cold Minimal Essential Medium (Gibco, Grand Island, N.Y.) supplemented with penicillin-streptomycin (2×, Gibco, Grand Island, N.Y.). After trimming axons and connective tissue, ganglia were transferred into enzyme solution, i.e., Hank's Balanced Salt Solution containing 5 mg/ml collagenase (Type 2, Worthington, Lakewood, N.J.), and incubated for three hours at 5% $CO_2$-95% $O_2$ 37° C. A pellet was subsequently obtained by repeated trituration through flame-polished glass pipettes and centrifuged at 50×g for 10 minutes. Single cells were resuspended and plated onto poly-1-ornithine (Sigma) coated coverslips with neurobasal media (Gibco) supplemented with albumin solution (0.7%, Sigma), penicillin-streptomycin (2×), B27 with retinoic acid (2×, Invitrogen), beta-mercaptoethanol (0.11 mM, Gibco), mouse nerve growth factor (0.04 g/ml, Promega, Madison, Wis.) and L-glutamine (2×, Gibco). Recombinant TGF-β1 and TGF-β2 (Calbiochem, cat #616455, PF017) were dissolved in 10% ethanol in phosphate buffered saline (PBS) to yield a stock concentration of 10 ng/μl. TGF-β1 or TGF-β2 (10 ng/ml) was added to cultures at the beginning of incubation at 37° C. 5% $CO_2$-95% $O_2$.

Transgenic mice. To decrease the response to TGF-β specifically in astrocytes, we took advantage of a dominant negative mutation in the type II TGF-β receptor that has been cloned into a bidirectional doxycycline-regulatable element (bi-tetO) that also drives enhanced green fluorescent protein (GFP). Andrews, Z. B. et al., 2006 Neurobiol Dis. 21, 568-75.

TetO-TBR2-DN mice were obtained from Jackson Laboratories, Bar Harbor, Me. This line was crossed to a GFAP-tTA transgenic line (Jackson Laboratories). This line confers expression of tetO transgenes to astrocytes in the absence of doxycycline, and is induced by injuries, including stroke. DRGs were dissected from these mice and cultured as above.

DRG Immunohistochemistry. Rats were perfused transcardially with 200 ml saline followed by 500 ml 4% paraformaldehyde in PBS. DRGs were removed and embedded in OCT. Sections were cut by cryostat in a thickness of 8 μm and, after blocking with 15% BSA, incubated with the first primary antibodies for 12 hrs at 4° C. as indicated, i.e., anti-TGF-βRI rabbit polyclone (1:100, AbCam, ab31013), anti-TGF-βRII goat polyclone (1:100, Santa Cruz, sc-33932), PGP 9.5 rabbit or chick polyclonal (1:200, AbCam), GFAP rabbit polyclonal (1:200, AbCam). For co-localization studies, two primary antibodies from goat and rabbit were respectively designed with secondary antibodies using donkey anti-goat antibody Alexa Fluor 488, donkey anti-rabbit antibody Alexa Fluor 594 (1:200, Invitrogen). For immunochemistry of DRG cells in culture, labeling with antibodies to TGF-βRI and RII was carried out by successively incubating those two primary antibodies for 90 minutes followed by the secondary antibody for another 90 minutes at room temperature. All samples were mounted with DAPI nucleic acid stain and imaged with a fluorescence microscope (Nikon Eclipse, Ti-S) with corresponding excitation wavelength appropriate for 488, 594 and DAPI nucleic acid stain.

Electrophysiology. Whole-cell voltage patch-clamp recordings were conducted at room temperature (22-23° C.) on the stage of an inverted phase contrast microscope (Nikon Inc., Melville, N.Y.). The recording pipettes were pulled from borosilicate glass to give final resistances of 2-6Ω. Data were acquired with Digidata interface (1200 series, Axon Instruments) and pClamp software (version 9.1, Axon Instruments). The concentrations of the electrode solutions (in mM) used in these experiments were as follows: for recording action potential, $K^+$ current and non-selective cationic current (pH adjusted to 7.3-7.4 using KOH): potassium gluconate (115), KCl (25), NaCl (5), HEPES (10), CaCl (1), EGTA (1.12) and ATP-Mg (2); for recording $Na^+$ current (pH adjusted to 7.3-7.4 using NaOH): CsF (110), $MgCl_2$ (5), EGTA (11), NaCl (10) and HEPES (10). The cells were bathed in modified Tyrode saline consisting of (in mM): NaCl (135), KCl (5.4), $MgCl_2$ (1), $CaCl_2$ (2), $NaH_2PO_3$ (0.1), HEPES (10) and glucose (10). The osmolality was maintained at 280-300 mOsm for the intracellular electrolyte and 300-330 mOsm for the extracellular bath solution. Agents such as capsaicin, capsazepine, TEA, 4AP, TTX etc were delivered through a valve control system (BPS-4, Scientific Instrument, New York). Prior to patch clamping a cell, the amplifier (Axopatch 200B, Axon Instruments, CA, USA) was zeroed so that any junction potential was balanced by an offset potential. High resistance (Gigaohm) seals were formed between the recording electrode and cell membrane and ruptured by suction using standard patch clamp recording methods. Action potentials were recorded in mode of I-clamp after observed membrane potential setting at I=0, and the currents were recorded by switching mode to v-clamp. The current signals were recorded to disk for off-line analysis using pCLAMP fit and Origin 7. Results were expressed as means±SE, n=number of cells.

Results.

Figure 2:
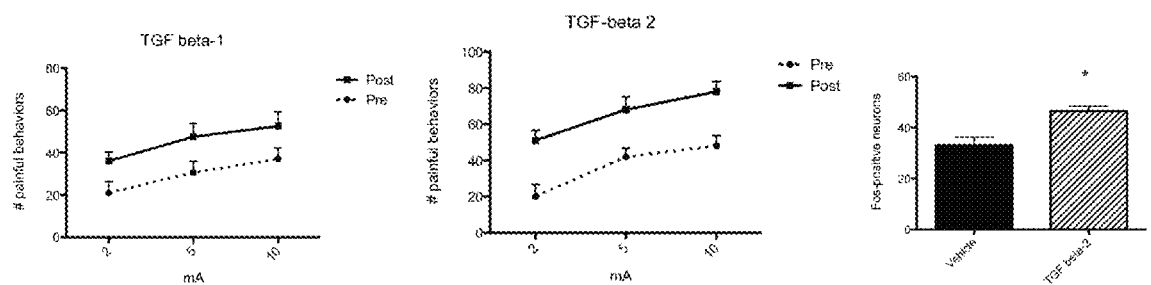
FIG. 2 illustrates that TGF-β induces pain in conscious rats, and blockade of TGF-β reduces pain in rats with chronic pancreatitis.
Figure 2:
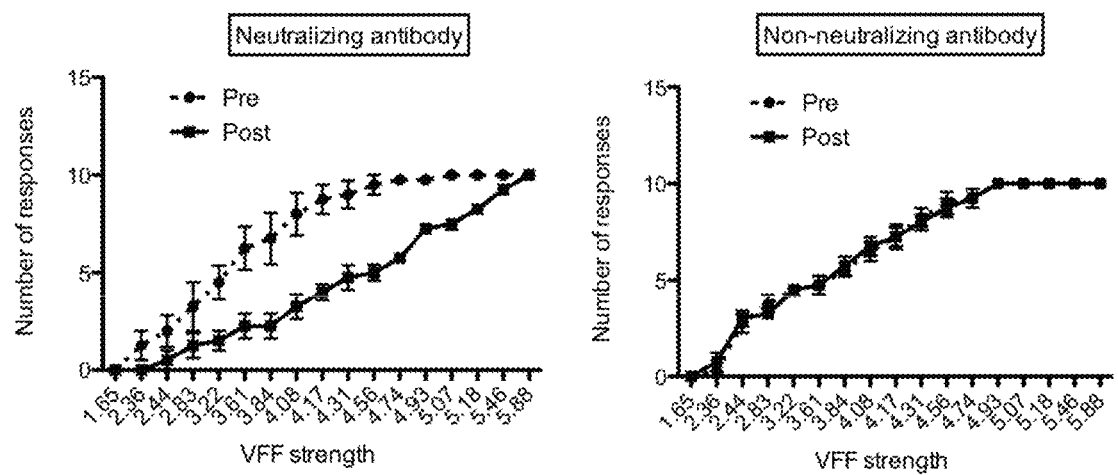
Figure 2:
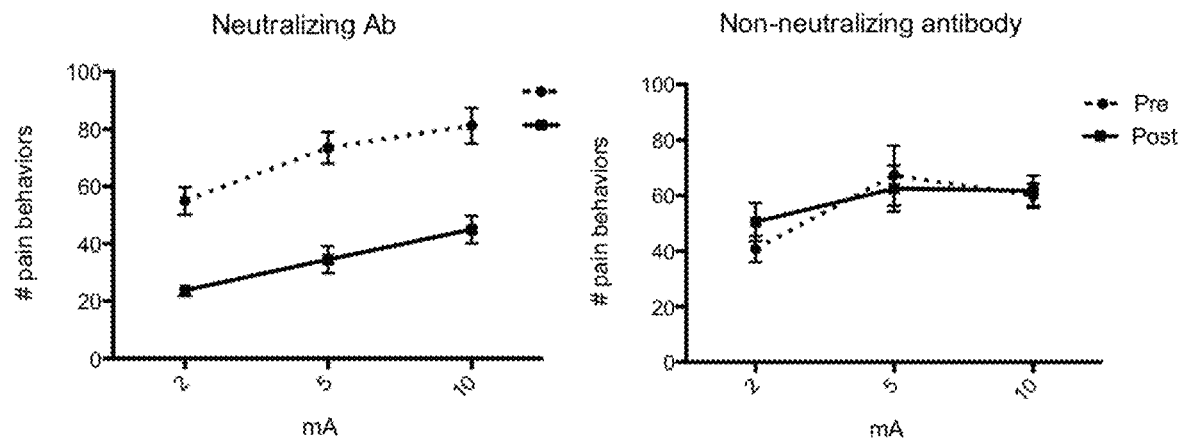

TGF-β receptors were expressed on sensory neurons in rat dorsal root ganglia (DRG), as can be seen in FIG. 1. TGF-βRI and -βRII were vigorously expressed in dorsal root ganglion (DRG) sections (FIGS. 1A-C), and several observations could be made about their staining pattern. First, they were expressed by both neurons and glia, as evidenced by co-expression of PGP9.5 and GFAP, respectively. Secondly, both receptors were extensively co-localized with each other. Finally, these receptors were predominantly expressed in small size neurons (~30 μm diameter). Neurons in DRG cultures also stained strongly for both TGF-βRI and -βRII (FIG. 1D). TGF-β induced pancreatic hyperalgesia (increased sensitivity to pain) in vivo and contributed to pain behavior in a rat model of chronic pancreatitis (FIG. 2). Intra-pancreatic infusion of either TGF-β1 or TGF-β2 resulted in a hyperalgesic behavioral response to noxious stimulation (electric stimulation, ES; top left and middle panels). Further, TGF-β2 intra-pancreatic infusion (TGF-β1 was not tested in this assay) followed by ES resulted in greater FOS expression in the spinal cord (top panel, right). FOS protein is routinely used as a marker of noxious stimulation.

Subsequent blockade of TGF-β with a monoclonal TGF-β neutralizing antibody, but not with a monoclonal TGF-β non-neutralizing antibody, reduced pain in rats with chronic pancreatitis. As can be seen in FIG. 2 (bottom two panels) the neutralizing anti-TGF-β antibody caused a significant reduction in pain from baseline, as measured by both pain behaviors in response to Von Frey Filament (VFF) as well as electric stimulation. On the other hand, the non-neutralizing anti-TGF-β antibody did not change behavior at all.

Figure 3:
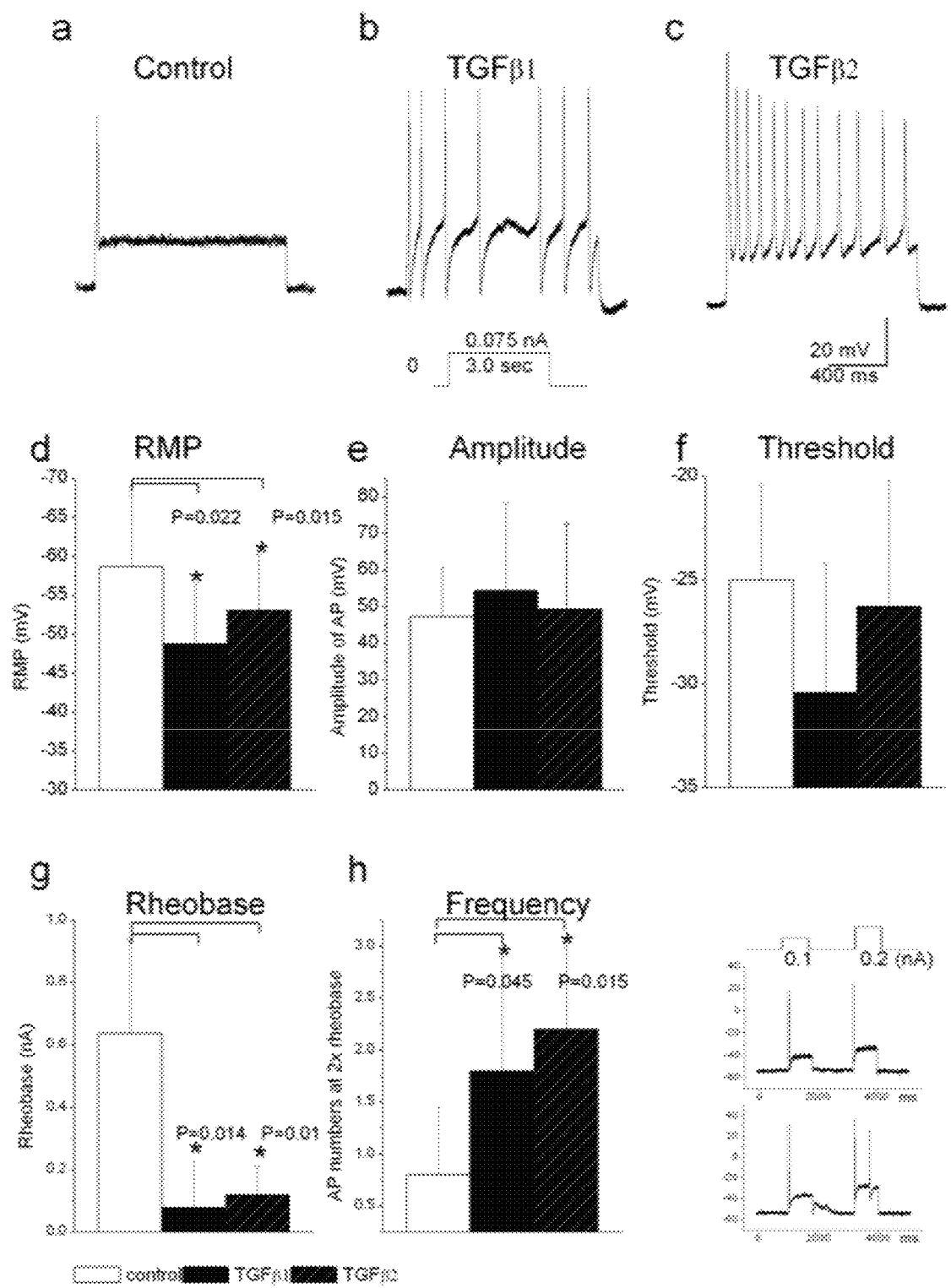
FIG. 3 and FIG. 4 illustrate that TGF-β induces excitability of isolated sensory neurons.
Figure 4:
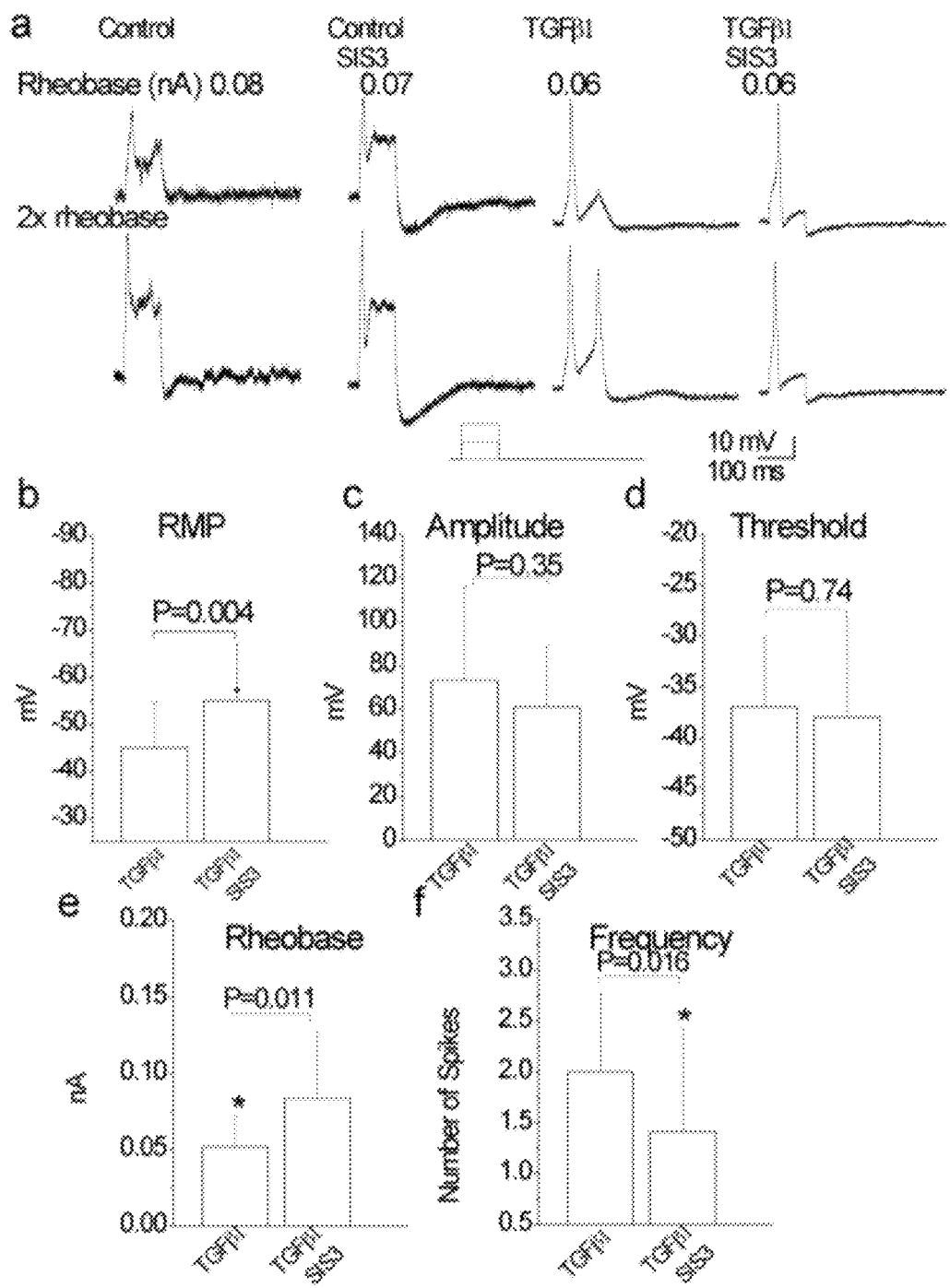

TGF-β induced excitability of rat DRG neurons in vitro in a Smad-dependent manner (FIGS. 3 and 4). Neurons in DRG cultures were measured whole-cell (i=0) mode. The resting membrane potential (RMP) of neurons from cultures exposed to TGF-β (n=21) was significantly lower than controls (n=25), i.e., −48.8±7.6 mV versus −58.7±9.2 mV; P=0.02. To determine rheobase, threshold and firing frequency, multi-step depolarizing current pulses were used while holding the cell to near the average membrane potential. Spontaneous spike trains were often seen in neurons treated with TGF-β but rarely seen in control neurons (FIG. 3 a-c) with a significant increase in the proportion of tested cells showing multiple action potentials (43% versus 14%; P=0.03). The current pulse (rheobase) required for triggering an action potential was also significantly lower in neurons treated with TGF-β as compared with controls (0.15±0.09 versus 0.64±0.4 nA; n=11 each; P=0.01) (FIG. 3 d-h). Further, the number of action potentials evoked by two times rheobase current stimulation was significantly higher in TGF-β treated neurons (2.75, 1.5 Hz; n=17) as compared with controls (1.3, 0.5 Hz; n=56) (FIG. 4 a-f).

FIG. 4 shows that the effects of TGF-β on neuronal excitability were dependent on the SMAD pathway thus affirming the potential use of Smad inhibitors for treatment of pain as well.

Figure 5:
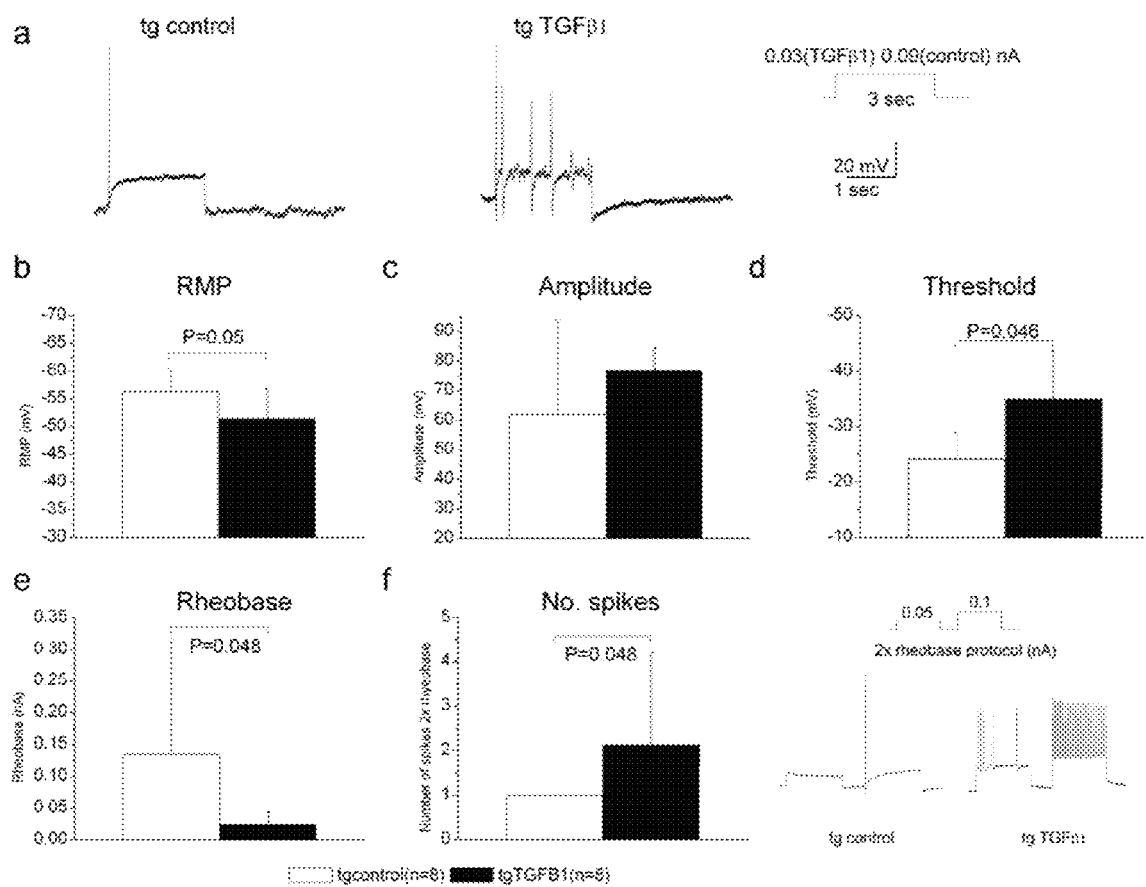
FIG. 5 illustrates that the effects of TGF-β on excitability do not require glial participation.

The effects of TGF-β on DRG neuronal excitability do not require glial participation (FIG. 5). Since both glial and neuronal cells in the DRG preparations can respond to TGF-β, we determined the effects of exogenous TGF-β on DRG neuronal excitability in preparations from mice that lacked the TGF-βI receptor in glia. In these preparations, TGF-β treatment (10 ng/ml) also resulted in a lower RMP (−49.7±5.5 mV versus −54.5±4.94 mV in tg-control (n=4)). Exposure to TGF-β1 induced a trend for increase in spikes, i.e., 2.8±1.5 in TGF-β1 (n=7) and 1.3±0.23 in non-TGF-β1 (n=8), at the same stimulation. There were decreases in firing threshold, i.e., −35 mV in TGF-β1 (n=7) and −22 mV in non-TGF-131 (n=8), and rheobase, i.e., 0.03 nA in TGF-β1 and 0.11 nA in non-TGF-β1, as the results of TGF-β1 treatment. On average, there were no obviously different changes in excitability measurements between tg-TGF-β1 and WT-TGF-β1, indicating the increase in DRG neuronal excitability induced by TGF-β did not require glial participation.

Figure 6:
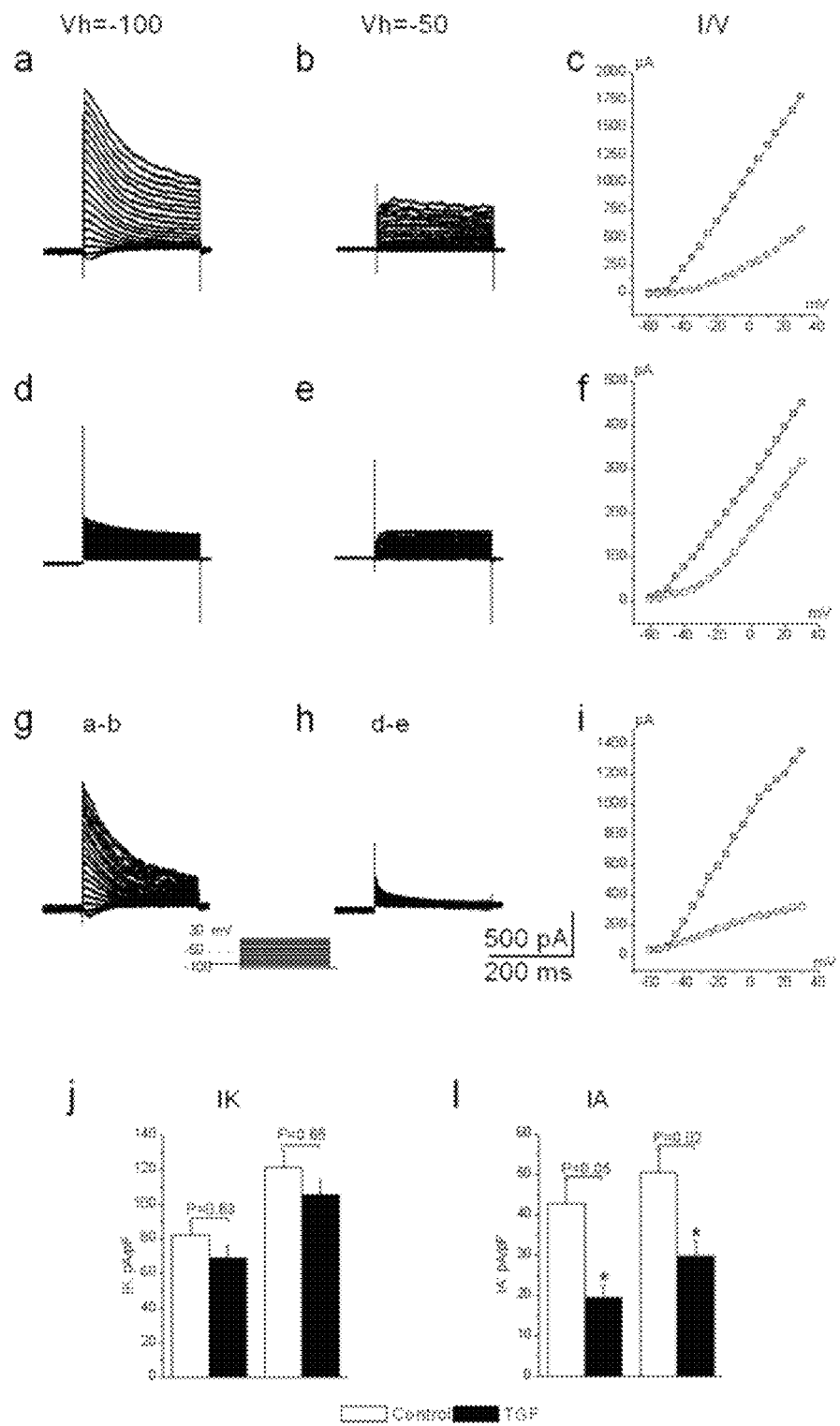
FIG. 6 illustrates that TGF-β influences $K^+$ channel activity.
Figure 7:
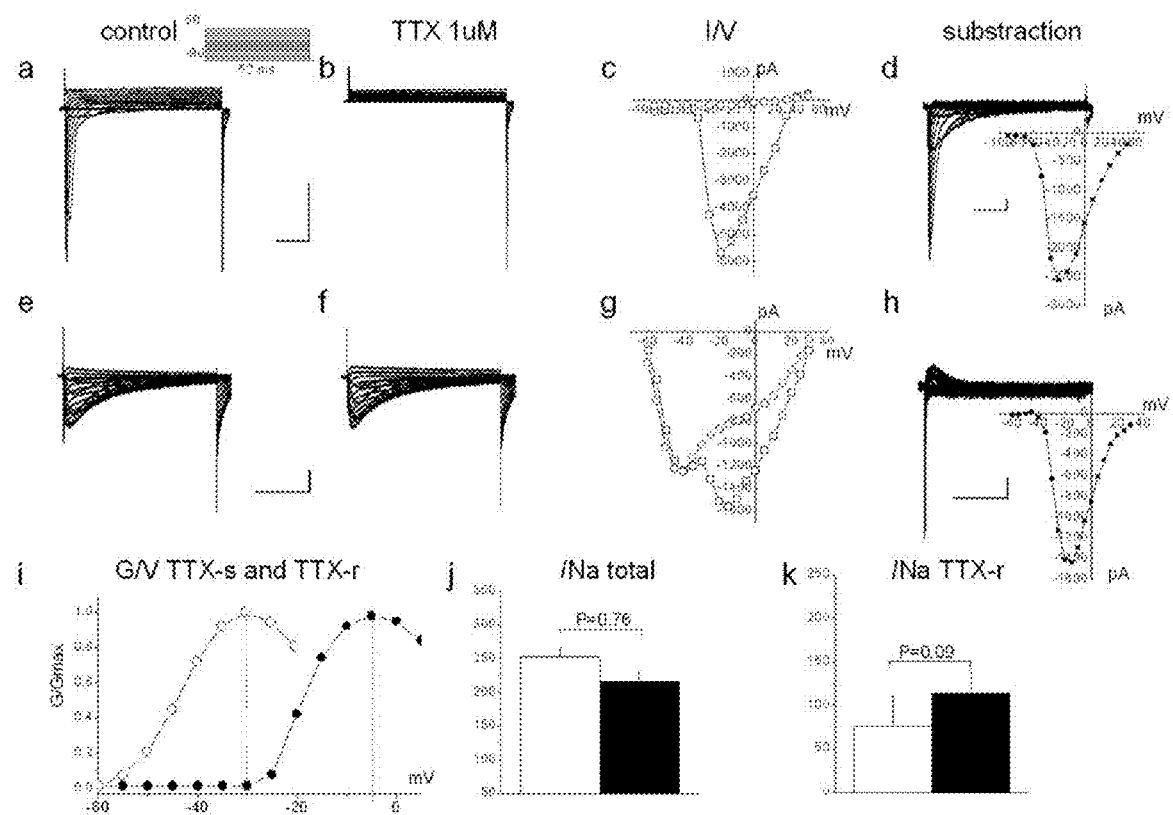
FIG. 7 illustrates that TGF-β influences $Na^+$ channel activity.

TGF-β influences $K^+$ and $Na^+$ channel activity (FIGS. 6 and 7). Voltage-dependent potassium (Kv) currents play a fundamental role in determining neuronal excitability. We examined the possibility that TGF-β treatment affects Kv currents in DRG neurons. Two important voltage-dependent $K^+$ currents are the transient A-type current ($I_A$) and the sustained delayed rectifier type current ($I_K$). FIG. 6a shows a step depolarization protocol from −100 to +30 mV in 5-mV increments with a duration of 400 ms to activate all Kv channels ($I_{total}$) in DRG neurons in culture. The peak current voltage (I/V) curves are shown in FIG. 6c. TGF-β treatment did not result in a significant reduction of $I_{total}$ density (pA/pF). Manipulating the holding membrane potential at −50 mV and starting depolarization steps from −50 to +30 mV in 5-mV increments with durations of 400 ms activated most of the sustained Kv channels but not A-type Kv channels (FIGS. 6, b and e). Subtraction of $I_K$ from $I_{total}$ yields $I_A$ (FIGS. 6, g and h). $I_A$ was further confirmed by the application of the A-type channel blocker 4-aminopyridine (4-AP; 5 mmol/L, data not shown) and a reversal potential of around −74 mV, close to $K^+$ equilibrium. The peak I-V curves of $I_A$ and the reduction from TGF-β treated neurons are shown in FIG. 6i. TGF-β treatment resulted in a remarkable reduction in $I_A$ density at +30 mV (29.6±3.8, n=10 versus 50.5±5.7, n=7 controls; P=0.02). Further, 11 of 22 tested TGF-β treated neurons showed an absence of $I_A$ current as compared with 2/16 control neurons (P=0.04).

Referring to FIG. 7, we also tested the effects of TGF-β on sodium channel activity. Nociceptive neurons have both tetrodotoxin-sensitive ($TT_XS$) channels (common to most neurons and responsible for a fast, rapidly inactivating current) and tetrodotoxin-resistant ($TT_XR$) channels, whose presence is associated with the ability to fire long trains of action potentials and, hence, increased excitability. Both types of current were identified in neurons. The densities of total $I_{Na}$ were 252.98±12.94 in control (n=16) and 216.12±15.01 in TGF-β (n=23; P=0.79); those of $TT_XR$ were 76.34±33.65 in control (n=6) and 114.25±27.32 in TGF-β (n=7; P=0.09).

Figure 8:
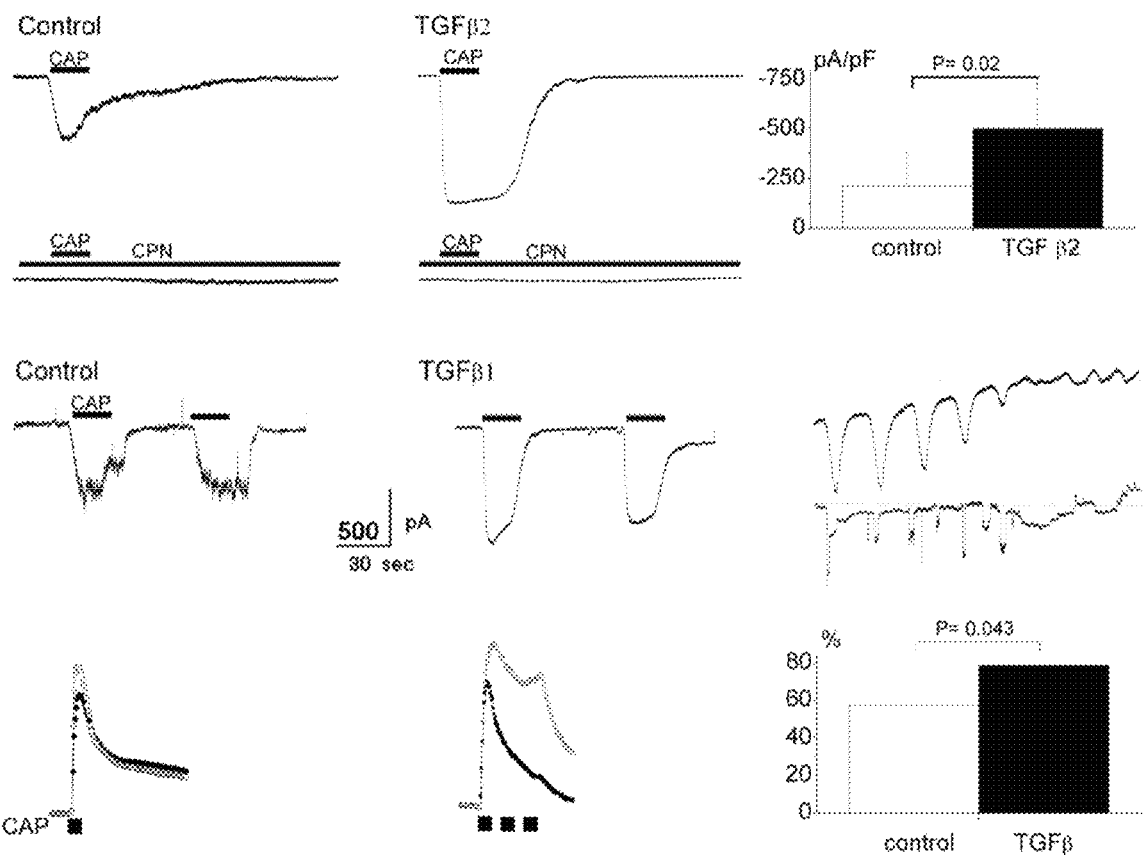
FIG. 8 illustrates that TGF-β enhances the activity of the transient receptor potential vanilloid 1 (TRPV1).

TGF-β enhanced the rat DRG neuronal response to transient receptor potential vanilloid 1 (TRPV1) activation in vitro (FIG. 8). The TRPV1 receptor is a key molecular integrator for physical and chemical noxious stimuli. Sensitization of this receptor, widely expressed on nociceptor neurons, enables this channel to be active at physiological temperatures, leading to increased spontaneous afferent activity. In this study, TRPV 1 activity was evaluated as the response to capsaicin (CAP) application, which resulted in a non-selective cationic inward current. CAP application to middle sized (25-35 μM) neurons resulted in a slowly activating and sustained inward current, which desensitized during washout and was suppressible by the TRPV1 antagonist capsazepine (CPN), as seen in FIG. 8. Capsaicin induced significantly largely currents in neurons treated with TGF-β (724.7±129.4, n=17 versus 336±43.7 pA in controls, n=35; P=0.02).

SUMMARY

We have found that TGF-β induces pain in conscious rats. Having shown that TGF-β is capable of activating sensory neurons in vitro, we demonstrated its effects in vivo. TGF-β was infused in the pancreatic duct of live rats and their response studied to electrical stimulation of the pancreas, a standard method for inducing pain. Our results indicate that TGF-β significantly enhanced the pain response in conscious rats.

We moreover found that blockade of TGF-β reduced pain in rats with chronic pancreatitis. To confirm that TGF-β actually contributed to pain, we administered a monoclonal TGF-β neutralizing antibody systemically to rats with chronic pancreatitis, a condition which is associated with fibrosis and pain. One week after infusion, the neutralizing anti-TGF-β antibody caused a significant reduction in pain from baseline, as measured by both pain behaviors in response to electric stimulation as well as by Von Frey Filament (VFF) testing, which directly measures abdominal wall sensitivity to touch. Administration of a control monoclonal TGF-β non-neutralizing antibody did not improve pain when tested in a similar manner.

TGF-β is known to be increased in the pancreas with chronic inflammation; here we showed that TGF-β receptors are expressed by nociceptors, TGF-β infusion into normal pancreas induces hyperalgesia to pancreatic stimulation, and TGF-β antagonism attenuates hypersensitivity and hyperalgesia in chronic pancreatitis.

Example 2

TGF-Beta Antagonists SB431542 and SIS3 Effective in Preventing Decrease of Resting Membrane Potential Induced by TGF-Beta In further studies, the effects of TGF-β (10 ng/ml) on resting membrane potential (RMP) in the presence or absence of the TGFβRI/ALK5 kinase inhibitor SB431542 (5 μM) (panel A: n=17, 24, 21 and 18 for the groups, respectively) or the SMAD3 inhibitor SIS3 (3 μM) (panel B: n=11 for TGF and n=13 for TGF+SIS3), both as further examples of TGF-β antagonists, were investigated. Dorsal root ganglion (DRG) neurons were incubated for 48 hours with the various agents, as indicated. Both inhibitors prevented the decrease in RMP induced by TGFβ.

Figure 9:
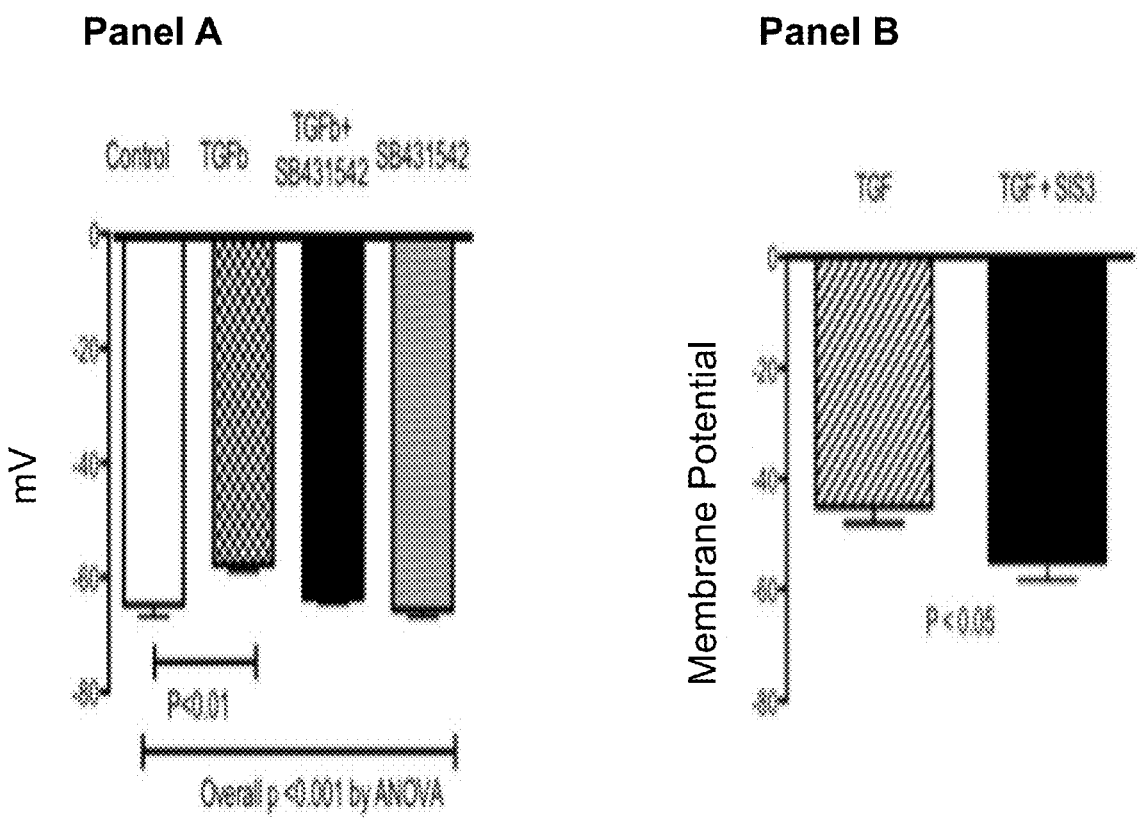
FIG. 9 illustrates that the effects of TGF-β on resting membrane potential are blocked by the TGFβRI/ALK5 kinase inhibitor SB431542 (see panel A) as well as by the Smad3 inhibitor SIS3 (see panel B).

SIS3 was dissolved in DMSO and diluted in culture media that was added at the time of plating with a final concentration of 3 μM. After one hour, the culture wells received TGF-β1 (0.2 ng/ml) for further incubation. Most cells were patched at 12-24 h, and both agents were refreshed daily if incubated for over 24 h. The results illustrated in FIG. 4 and in FIG. 9 show that SIS3 attenuate the TGF-β1 induced changes in resting membrane potential (RMP), rheobase and frequency of action potentials at 2× rheobase current.

As described in the examples, transforming growth factor-β (TGF-β) plays a significant role in pain. Targeting this molecule by molecules that block its action therefore represents an original approach to the treatment of pain and provides the basis for an entirely new class of analgesics.

What is claimed is:

1. A method for treating pain, comprising administering to a subject in need thereof a composition comprising a TGF-β antagonist in a therapeutically effective amount to treat pain, wherein said TGF-β antagonist is selected from the group consisting of TGF-β-neutralizing antibodies and fusion proteins thereof.

2. A method for reducing sensation of pain in a subject experiencing pain, comprising administering to said subject a composition comprising a TGF-β antagonist, wherein said TGF-β antagonist is selected from the group consisting of TGF-β-neutralizing antibodies and fusions proteins thereof, and whereby said TGF-beta antagonist is administered in an amount therapeutically effective to reduce excitability of said subject's nociceptors that have become hyperexcited upon activation by TGF-beta and, thereby, to reduce sensation of said pain.

3. The method of any of claim 1, or 2, wherein said TGF-β antagonist is a monoclonal TGF-β-neutralizing antibody.

4. The method of any of claim 1, or 2, wherein said TGF-β antagonist is a fusion protein comprising a monoclonal TGF-β-neutralizing antibody and an antibody against transient receptor potential Vanilloid receptor 1.

5. The method of any of claim 1, or 2, wherein said TGF-β antagonist is a fusion protein comprising a monoclonal TGF-β-neutralizing antibody and an antibody against TrkA.

6. The method of any of claim 1, or 2, wherein said TGF-β antagonist is a fusion protein comprising a monoclonal TGF-β-neutralizing antibody and an antibody against NGF.

7. The method of any of claim 1, or 2, wherein said TGF-β antagonist is an engineered TGF-β-neutralizing antibody selected from the group consisting of chimeric antibodies, de-immunized antibodies, humanized antibodies, Fab or scFv antibody fragments, multimeric scFvs, and fully human antibodies.

8. The method of any of claim 1, or 2, wherein said TGF-β antagonist is a TGF-β1 antagonist.

9. The method of any of claim 1, or 2, wherein said pain is pain in inflammatory disease.

10. The method of claim 9, wherein said inflammatory disease is a member selected from the group consisting of rheumatoid arthritis, diabetic neuropathy, intestinal inflammation of ulcerative colitis or Crohn's disease, radiation-induced fibrosis, pancreatitis, and myocarditis.

11. The method according to claim 10, wherein said inflammatory disease is rheumatoid arthritis.

12. The method according to claim 10, wherein said inflammatory disease is diabetic neuropathy.

13. The method according to claim 10, wherein said inflammatory disease is intestinal inflammation of ulcerative colitis or Crohn's disease.

14. The method according to claim 10, wherein said inflammatory disease is radiation-induced fibrosis.

15. The method according to claim 10, wherein said inflammatory disease is pancreatitis.

16. The method according to claim 10, wherein said inflammatory disease is myocarditis.

17. The method of any of claim 1, or 2, wherein said pain is pain in cancer.

18. The method of any of claim 1, or 2, wherein said administration is local administration.

* * * * *